US005905093A

United States Patent [19]

Achkar

[11] Patent Number: 5,905,093

[45] Date of Patent: May 18, 1999

[54] FISH SCALE EXTRACT AS A CALCIUM SUPPLEMENT

[75] Inventor: John Achkar, Brooklyn, N.Y.

[73] Assignees: Nadia Achkar, Brooklyn; Robert B. Zeinoun, Armonk, both of N.Y.

[21] Appl. No.: 09/025,003

[22] Filed: Feb. 17, 1998

[51] Int. Cl.[6] .................................................... A01N 25/00

[52] U.S. Cl. .......................... 514/784; 514/905; 424/522; 426/531; 426/542; 426/655

[58] Field of Search .................................... 426/531, 542, 426/655; 514/784, 905; 424/522

[56] References Cited

U.S. PATENT DOCUMENTS 5,422,099 6/1995 Hollick et al. ............................ 424/59
5,698,222 12/1997 Mazer et al. ............................ 424/464

FOREIGN PATENT DOCUMENTS 402245167 9/1990 Japan .
408107771 4/1996 Japan .
363049057 3/1998 Japan .

*Primary Examiner*—Thurman K. Page
*Assistant Examiner*—Lakshmi Channavajjala
*Attorney, Agent, or Firm*—Cohen, Pontani, Lieberman & Pavane

[57] ABSTRACT

The present invention is directed to a calcium rich preparation which is prepared by soaking fish scales in an acidic solution for a defined period of time. This fish scale extract can be used as food supplement to prevent or reduce the risk of bone loss or other calcium deficiencies. The calcium form in this fish scale extract can be readily absorbed by the skin.

3 Claims, No Drawings

FISH SCALE EXTRACT AS A CALCIUM SUPPLEMENT

BACKGROUND OF THE INVENTION

1. Field of the Invention

This invention relates to a novel material and composition useful as a calcium supplement for humans and other animals. In particular, this invention relates to a fish scale extract containing a special form of calcium which can be applied topically to the skin and absorbed easily by the skin for strengthening bones or preventing other calcium deficiencies.

2. Description of the Related Art

Calcium is the fifth most abundant element in the human body. It plays an important role in many physiological processes, including nerve and muscle functions. Not surprisingly, nutritional and metabolic deficiencies of calcium can have broad-ranging adverse effects. Since about 90% of the body's calcium is found in bone tissues, many of these adverse effects are manifested through deficiencies in the structure, function and integrity of the skeletal system.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is idiopathic "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures occur often, for example, in the wrist, hips and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling occurs in a series of discrete pockets of activity in the bone, called "osteoclasts" and "osteoblasts". Osteoclasts (bone dissolving or resorting cells) are responsible for the resorption of a portion of bone within the bone matrix, during the resorption process. After resorption, the osteoclasts are followed by the appearance of osteoblasts (bone forming cells), which then refill the resorbed portion with new bone.

In a healthy adult, the rate at which the osteoclasts and osteoblasts are formed maintains a balance of bone resorption and bone formation. However, in osteoporotics an imbalance in this remodeling process develops, resulting in loss of bone at a rate faster than the accretion of bone. This imbalance is much more severe, and occurs at a younger age, in osteoporotics as compared to healthy adults.

Many compositions and methods are described in the medical literature for the prevention or "treatment" of osteoporosis. Many of these compositions and methods attempt to either slow the loss of bone or to produce a net gain in bone mass. See, for example, R. C. Haynes, Jr. et al., "Agents affecting Calcification", The Pharmacological Basis of Therapeutics, 7th Edition (A. G. Gilman, L. S. Goodman et al., Editors, 1985); and G. D. Whedon et al., "An Analysis of Current Concepts and Research Interest in Osteoporosis", Current Advances in Skeletogenesis (A. Ornoy et al., Editors, 1985). Estrogen is often used to affect the metabolism of calcium. Treatments using fluoride have also been described. However, the utility of such agents may be limited, due to possible adverse side effects. See W. A. Peck, et al., Physician's Resource Manual on Osteoporosis (1987), published by the National Osteoporosis Foundation (incorporated by reference herein).

Nutritional therapies for osteoporosis or prevention for other calcium deficiencies have also been proposed. Many calcium-containing compounds and compositions have been described for use as nutritional supplements. Many commercial preparations are also available, typically containing calcium carbonate. Calcium chloride, calcium gluceptate, calcium gluconate, calcium lactate, calcium phosphate, calcium citrate, and other calcium salts have also been described for use in calcium supplements. The use of calcium citrate, for example, is described in French Patent 2,219,778, Monteau, published Sep. 27, 1974; and World Patent Publications 86/04814 and 86/04815, Pak et al., both published Aug. 28, 1986. Food supplements containing calcium citrate malate are described in Japanese Patent Document 56/97, 248, Kawai, published Aug. 5, 1981.

The utility of these known supplements varies. Unlike agents (such as estrogen) which affect the metabolism of bone, calcium nutritional supplements have been thought to provide a source for calcium. Not every calcium compound can be absorbed and metabolized by the body. Applicant believes that the degree of calcium adsorption depends on the forms of the calcium compounds. Insofar as applicant knows, no prior art teaches or suggests calcium in a form of an acid extract from a natural product to be used as a absorbable calcium supplement.

It is now discovered that an extract from fish scales contains a special form of calcium complex that is useful as food supplement or a portion of a food supplement to provide the users with more calcium than they otherwise have available from their normal diets. This fish scale extract can be easily absorbed by the human body through the skin.

Many commercial calcium supplement preparations also contain vitamin D to facilitate calcium absorption, as in the instance of milk. It is well known that vitamin D plays an active role in calcium homeostasis and is a major regulator of the concentration of $Ca^{2+}$ in plasma.

The concept of topical application of calcium supplements has never been suggested or reported. However, topical application of calcium supplement can be unique and useful as an alternative route to provide the body with calcium supplementation, particularly if the calcium is in a form that can be readily absorbed by the skin. The fish scale extract in the present invention is one of those forms. It should be noted that vitamin D is also synthesized in the skin, suggesting that vitamin D may directly or indirectly interact with calcium to facilitate the absorption of calcium from the skin or otherwise participate calcium metabolism after the absorption.

SUMMARY OF THE INVENTION

An object of the present invention is to provide a method of obtaining a calcium complex in which calcium is associated with one or more of other organic molecules. In particular, the calcium complex is obtained by extracting it from fish scales with an acidic solution containing preferably a hydrocarboxylic acid or acetic acid or a mixture of the two.

Another object of the present invention is to provide a method of administering the calcium complex or extract identified by the extraction process through a topical application. The calcium complex can be readily absorbed through the skin.

A further object of the present invention is to provide a food supplement for preventing or reducing calcium deficiency or the risk of bone loss such as occurs in osteoporosis and related disorders.

Other objects and features of the present invention will become apparent from the following detailed description.

DETAILED DESCRIPTION OF THE PRESENTLY PREFERRED EMBODIMENTS

Turning now to the first embodiment, the materials used in the extraction process comprise fish scales, a hydrocarboxylic acid or acetic acid, or preferably, a mixture of the two. The fish scales may be collected from any type of fish in any amount. Preferably, for a preparation of 500 ml, 1 oz of fish scales are required. The fish scales are first briefly, lightly sprayed with fresh water and then they are soaked in an organic acidic solution. Preferably, the substance coating each of the fish scales is not removed by spraying. Any organic acidic solutions, preferably, a hydrocarboxylic acid such as citric acid or tartaric acid, or acetic acid, may be used for soaking the fish scales. The acidic solution may be prepared at a concentration of about 0.1N to about 1N or at a concentration which is comfortable to the skin. A buffer system such as PBS at a pH of about 2–3 or comfortable to the skin may also be employed in place of the acid. Most preferably, the acidic solution is made of a mixture of a hydrocarboxylic acid and acetic acid at a preferred ratio of 2:3. The ratio of the hydrocarboxylic acid and acetic acid may vary depending on the intended use. Once the acidic solution is formed, the fish scales are introduced into the solution in such a way that the fish scales are completely immersed in the solution. The container that contains the fish scales soaked in the acidic solution is then covered and kept at room temperature for at least 12 hours, preferably, about 5 days, during which the calcium or calcium complex continuously comes out of the fish scales. Most preferably, the fish scales may be maintained in the solution until a equilibrium of the calcium concentration between the fish scales and the acidic solution is established so that the calcium concentration is maintained at a constant level. This process may be accelerated by heating the solution. The presence and concentration of the calcium in the solution can be readily determined by a person skilled in the art.

Alternatively, food products such as lemon or lime juice and vinegar may be used to substitute the hydrocarboxylic acid and acetic acid. In such case, about 1 oz of the fish scales are soaked in about 500 ml of lemon or lime juice, or in about 500 ml of vinegar, preferably white vinegar or red wine vinegar, or in a mixture including about 200 ml of lemon or lime juice and about 300 ml of vinegar, for at least 12 hours, preferably about 5 days.

After the fish scales have been sufficiently soaked in the solutions as described above, considerable amount of calcium or calcium complexes from the fish scales are dissolved or associated with the compounds in the acidic solution to form complexes. This preparation may then be filtered by a mesh or a screen so as to separate the fish scales from the fish scale extract that contains calcium associated with one or more other organic molecules.

The extract so prepared is then suitable for an immediate use or may be further modified as a food supplement. For example, an extract cocktail may be formed by adding some other substances such as garlic and honey, etc. into the extract. Alternatively or additionally, vitamin D may be added to the extract. For an extract containing about 500 mg of calcium, about 200 International Units of vitamin D may be added. The extract may also serve as a major component for a pharmaceutical composition.

In another embodiment, the fish scale extract may be dried by any suitable means, such as lyophilization for the purpose of storage or shipment. The dried fish extract may be resuspended or dissolved in a pH neutral solution, or manufactured in the form of capsules or tablets.

In case of an immediate application after the extraction, the extract may be administered topically or orally. For an orally administration, the extract can be taken alone or combined with other foods. At least a tea spoon of the extract or its modification may be employed daily depending on the user's needs or for as long as the user desires. Preferably, the extract or its modification is administered three times a day and one tea spoon at each time. For a topical application, the extract or its modification may be applied directly to various areas of the skin such as the face or the chest at least once a day or as often as the user desires or depending on the user's symptoms.

The extract, when administered either orally or topically, may be useful to prevent, or reduce the risk of, the occurrence of bone loss such as osteoporosis or other calcium deficiencies.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method of administering a fish scale extract produced by soaking fish scales in an organic acidic liquid which comprises an organic acid selected from the group consisting of a hydrocarboxylic acid, acetic acid and the mixtures thereof, comprising topically applying said fish scale extract to the skin of a human body.

2. A method of administering a fish scale extract being produced by soaking fish scales in a liquid selected from the group consisting of lemon juice, vinegar and the mixtures thereof, comprising topically applying said fish scale extract to the skin of a human body.

3. The method in claim 1 or claim 2, wherein said fish scale extract comprises 500 mg of calcium and 200 international units of vitamin D.

* * * * *